United States Patent [19]

Buehler et al.

[11] 4,282,381
[45] Aug. 4, 1981

[54] PROCESS FOR PURIFYING HEXAMETHYLENEDIAMINE

[75] Inventors: Oscar R. Buehler, Newark; Harold F. Porter, Hockessin, both of Del.

[73] Assignee: E. I. Du Pont de Nemours and Company, Wilmington, Del.

[21] Appl. No.: 179,949

[22] Filed: Aug. 21, 1980

[51] Int. Cl.³ ............................................. C07C 85/26
[52] U.S. Cl. ..................................... 564/498; 260/707
[58] Field of Search ................................. 564/498, 492

[56] References Cited

U.S. PATENT DOCUMENTS

| | | | |
|---|---|---|---|
| 2,889,256 | 6/1959 | Campbell | 564/498 X |
| 2,987,452 | 6/1961 | Campbell et al. | 564/498 X |
| 3,193,472 | 7/1965 | Isacks | 564/498 X |
| 3,370,082 | 2/1968 | Eisfeld et al. | 260/465.8 R |
| 3,696,153 | 10/1972 | Kershaw et al. | 564/492 |
| 3,801,370 | 4/1974 | Porter et al. | 134/25 R |
| 3,839,408 | 10/1974 | Arend et al. | 260/465.8 R |

Primary Examiner—John Doll

[57] ABSTRACT

Hexamethylenediamine (HMD) is purified by dissolving ammonia in crude molten HMD under pressure, directing the solution thus prepared to a reduced pressure zone where the ammonia is vaporized thereby causing a portion of the HMD to crystallize following which the crystals in the slurry are washed with essentially pure HMD. This purified HMD is suitable for conversion into polyamide fibers.

8 Claims, 1 Drawing Figure

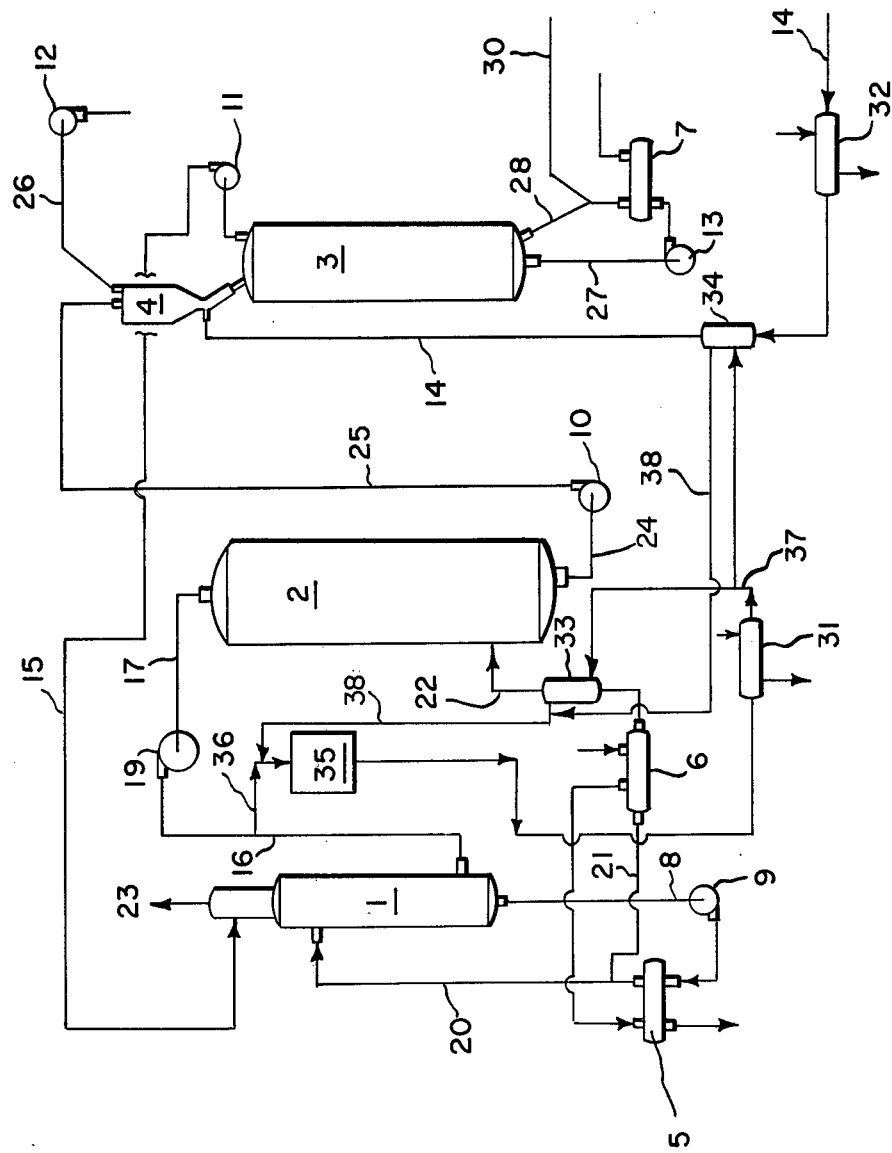

PROCESS FOR PURIFYING HEXAMETHYLENEDIAMINE

BACKGROUND OF THE INVENTION

1. Field of the Invention

This invention concerns the purification of hexamethylenediamine (HMD) using ammonia as an internal refrigerant to crystallize HMD from its melt. The crystals are then washed with refined molten HMD following which the crystals are melted and refined molten HMD is recovered.

2. Description of the Prior Art

The source of the hexamethylenediamine (HMD) which can be purified by the process of the present invention includes HMD from the catalytic hydrogenation of adiponitrile in the presence of ammonia using known catalysts, e.g., nickel, cobalt, or mixtures thereof usually precipitated on a finely divided carrier and Raney nickel catalysts. Exceptionally effective catalysts include iron compounds as disclosed in U.S. Pat. No. 3,696,153 issued Oct. 3, 1972 and assigned to E. I. du Pont de Nemours and Company. The process of the present invention is particularly suited for the purification of product produced by the iron catalyzed hydrogenation.

U.S. Pat. No. 3,370,082 issued on Feb. 20, 1968 discloses a method for the purification of adiponitrile which involves cooling the adiponitrile optionally with an internal coolant which is immiscible therewith, e.g., ethane, ethylene, propane and the like. The patentees suggest that the mother liquor adhering to the crystals which are separated after evaporation of the internal refrigerant can be displaced by washing with a suitable liquid including pure adiponitrile obtained from the melting of crystalline adiponitrile. Certain methods for recycle in a process for the purification of adiponitrile are disclosed in U.S. Pat. No. 3,839,408 issued on Oct. 1, 1974 and involve the continuous purification of adiponitrile by indirectly cooling crude adiponitrile in a crystallization zone, recovering the crystals from the crystallization zone, washing the crystals thus obtained with liquid adiponitrile, and returning the separated adiponitrile mother liquor to the crystallization zone. Although the patentees disclose the use of ammonia as a coolant, the use thereof is indirect, i.e., in heat exchange relationship with the adiponitrile and is not placed in direct contact with the nitrile.

The above discussed art does not suggest the use of ammonia as an internal refrigerant for the purification of HMD. Usually HMD has been purified by distillation. However, distillation is expensive and difficult because the impurities in the HMD and the HMD have very low relative volatilities. In addition, the elevated temperatures associated with distillation tend to accelerate decomposition of HMD.

SUMMARY OF THE INVENTION

The present invention provides a method for purifying hexamethylenediamine (HMD) which comprises absorbing a substantially anhydrous ammonia in a molten crude HMD in a first zone; transferring the solution thus obtained to a second zone wherein a portion of the ammonia dissolved in the molten material is vaporized and at least a portion of the molten HMD is crystallized following which the crystals are separated from the melt and washed in another zone using molten, refined HMD. In a preferred embodiment the crystals are separated from the molten hexamethylenediamine by settling in a fourth zone; washed countercurrently in the fourth zone, least a portion of the diamine used to wash the crystals is recycled to the first zone, the washed crystals of hexamethylenediamine are melted to provide the same refined hexamethylenediamine wash and thereafter a portion of the melted crystals of hexamethylenediamines which are not used for said wash is recovered.

DESCRIPTION OF THE DRAWING

The attached drawing depicts equipment for the continuous practice of the process of the present invention.

DETAILED DESCRIPTION OF THE INVENTION

A preferred source for the HMD which is purified according to the process of the present invention is from the hydrogenation of adiponitrile. A preferred hydrogenation involves contacting adiponitrile with hydrogen at a temperature of 110°–220° C. under a pressure of about 340 atmospheres in the presence of hydrogen, ammonia and an iron catalyst. This catalyst is obtained by reducing an iron oxide such as ferric oxide with hydrogen at a temperature up to 600° C. until such a time as the oxygen content of the oxide has decreased to less than 19% by weight. A typical analysis of hexamethylenediamine produced by the aforementioned technique is set forth in TABLE I.

TABLE I

| Compound | Amount (% by Weight) |
|---|---|
| E-aminocaproamide (ACA) | 0.01–0.02 |
| Adiponitrile (ADN) | 0.04–0.09 |
| 2-(aminomethyl) cyclopentylamine (AMC) | 0.01–0.03 |
| Bis (hexamethylene) triamine (BHMT) | 0.3–0.5 |
| Hydrogenation products of cyanoprene dimers (C-10) and/or decenedinitriles | 0.15–0.5 |
| 1,2-diamino cyclohexane (DCH) | 0:24–0.4 |
| Hexamethyleneimine (HMI) | 0.25–0.77 |
| Methylglutaronitrile (MGN) | 0.07–1.1 |
| Methylpentamethylenediamine (MPMD) | 0.07–1.1 |
| Epsilon-aminocapronitrile (N-112) | 0.2–0.5 |
| Ammonia (NH3) | 0.3 |
| n-hexylamine (NHA) | 0.4–0.5 |
| Pseudo-imine (PIA) | 0.02 |
| Tetrahydroazepine (THA) | 0.02–0.09 |
| Hexamethylenediamine (HMD) | Balance |

The process of the present invention uses crude diamine melt as feed. This means that the diamine and impurity comprise liquid phase and that there is no water or solvent intentionally introduced. Operation in this manner avoids the freeze point depression that accompanies the use of solvent and permits the process to operate at a higher temperature thereby reducing refrigeration. Crystallization from the melt also avoids the extra process step of purging contaminated solvent which in most cases requires a low temperature crystallizer and/or distillation.

A more complete understanding of the present invention may be had by referring to FIG. 1 attached hereto and made a part of the specification which depicts a preferred mode of operation of the process of the present invention. Alternate methods for performing the steps disclosed, e.g., ammonia absorption, crystallization and crystal washing should be apparent to those skilled in the art. With reference to the FIGURE, the principal equipment for the practice of the present process comprises absorber 1, crystallizer 2, displacement washing column 3, and in a particularly preferred embodiment, clarifier 4. Water fed heat exchangers 5, 6, 31 and 32, steam fed exchanger 7, and ammonia fed exchangers 33 and 34 control the temperature of the process streams. Fluid transfer is accomplished by pumps 9-13. In this embodiment, the crude HMD is introduced via line 14, into clarifier 4. The HMD which is to be crystallized by release of absorbed ammonia is introduced into the upper section of ammonia absorber 1 from the overflow of washing column 3 via pump 11 and line 15. The ammonia which is introduced via line 16 into absorber 1 is obtained from the off gas of crystallizer 2 (line 17) is compressed in compressor 19 prior to introduction into absorber 1. Makeup ammonia can be introduced at various locations, e.g., at the base of absorber 1 via line 16. A portion of the ammonia in line 16 is withdrawn via line 36, compressed in compressor 35, cooled in heat exchanger 31 to achieve liquification and then directed to heat exchangers 33 and 34 (line 37) whereby cooling is accomplished by vaporization of the liquid ammonia. The coolant discharge from condensers 33 and 34 is directed via line 38 to line 36. The diamine-ammonia solution is continuously removed from the base of absorber 1 via line 8 and passed through heat exchanger 5 to remove the latent heat of the ammonia and its heat of solution. A portion of the mixture thus cooled is returned to absorber 1 via line 20 while the remaining portion is passed via line 21 through heat exchanger 6 and 33 to crystallizer 2 via line 22. Under normal operation the pressure of the ammonia absorption column 1 is maintained in the range of 50 to 165 psia and preferably 80 to 140 psia and at a temperature in the range 25°-60° C. and preferably 35°-50° C. The diamine-ammonia solution is circulated and ammonia introduced until approximately 3 to 20% and preferably 6 to 10% ammonia is absorbed in the diamine melt. Any excess ammonia is vented from absorber 1 (line 23) and directed to a suitable recovery means (not illustrated). The diamine-ammonia solution leaving exchangers 6 and 33 is maintained at a temperature in the range 26 to 60 and preferably 30° to 40° C. prior to introduction to crystallizer 2. In any event, the temperature of the stream to crystallizer 2 is maintained above the freezing point of the impure diamine contained therein. The crystallization (cooling) is achieved by evaporating ammonia from the diamine-ammonia solution under a pressure in the range 5 to 40 and preferably 15 to 20 psia until approximately 15-30% of the molten diamine is crystallized. Preferably agitation is provided in the crystallizer. The slurry having the aforementioned solids level is continuously removed from crystallizer 2 (line 24) and passed through pump 10 and line 25 to clarifier 4. The molten HMD can contain up to 60% impurities but usually contains 25-35% impurities at this point and the crystals are in equilibrium with the melt. The slurry is contacted with the crude HMD introduced into the system via line 14 and the crystals pass downwardly into washing column 3. An apparatus especially useful for washing is disclosed in U.S. Pat. No. 3,801,370 issued on April 2, 1974. A portion of the molten HMD is removed from the top of clarifier 4 (line 26) to provide a purge of impurities from the system. The crystals slowly settle in wash column 3 and displace molten diamine which is produced by melting the HMD crystals reaching the bottom of the wash column 3 in a heating system comprising lines 27 and 28, pump 13 and heat exchanger 7. The molten diamine which is displaced by the crystals entering the top of the wash column 3 is removed from the wash column and directed via line 15 and pump 11 to the ammonia absorption column 1. Purified diamine melt at 60° C. is removed from the system via line 30. The wash column 3 preferably has internal sweeper bars. Maximum displacement of the impurities which cling to the surface of the molten diamine crystals is realized by maintaining wash column 3 essentially full of crystals. Purge 26 is sent to a suitable recovery system (not shown) in order to recover the diamine and any ammonia which is present. These compounds can be recycled to the process. Preferably the crystals are slightly subcooled relative to the diamine melt during washing. This subcooling is relieved by crystallization of some of the melt onto the crystals. During the entire crystal handling operations, care is taken to keep the crystal phase in equilibrium with the liquid phase by changing the temperature and impurity concentration slowly to avoid rapid crystallization which could cause agglomeration of crystals and plugging of the equipment. Satisfactory washing of the crystals is obtained when at least 60% and usually 70-95% of the crystals which reach the base of column 3 (all of which are eventually melted) are withdrawn from the system as refined product with the remainder being provided as a displacement wash as discussed hereinabove.

Ammonia, crude HMD (having the analysis approximating that set forth hereinabove) steam and cooling water etc. are introduced into the system which is lined out according to the foregoing disclosures and the flows and conditions set forth in TABLE II are obtained. At least 97% of the impurities in the crude HMD is removed in the process.

TABLE II

| Stream No. | 26 | 14* | 16 | 38 | 30 | 15 | 20 | 36 |
|---|---|---|---|---|---|---|---|---|
| Flow (Parts per hour) | 1 | 40 | 11 | ** | 38 | 245 | 420 | 8 |
| Temperature (°C.) | 60 | 70 | 30 | 50 | 60 | 36 | 47 | 37 |

*at inlet of heat exchanger 32
**flow of streams 16 and 38 total 11 pph.

We claim:

1. A process for the purification of hexamethylenediamine which comprises absorbing substantially anhydrous ammonia in molten crude hexamethylenediamine in a first zone, volatilizing a portion of the dissolved ammonia in a second zone to cool and thereby crystallize at least a portion of the hexamethylenediamine, separating the crystalline hexamethylenediamine from the molten hexamethylenediamine in a third zone, and thereafter washing the thus obtained crystalline diamine with refined molten hexamethylenediamine.

2. The process of claim 1 wherein the ammonia which is volatilized in the second zone is recycled to the first zone.

3. The process of claim 1 wherein molten crude hexamethylenediamine feed is introduced into the third zone and contacted with said crystalline hexamethylenediamine.

4. The process of claim 3 wherein the impurities are removed from the process along with a portion of the molten hexamethylenediamine from the third zone.

5. A process for the purification of hexamethylenediamine which comprises absorbing substantially anhydrous ammonia in molten crude hexamethylenediamine in a first zone, volatilizing a portion of the dissolved ammonia in a second zone to cool and thereby crystallize at least a portion of the hexamethylenediamine, separating the crystalline hexamethylenediamine from the molten hexamethylenediamine in a third zone, displacement washing the thus obtained crystalline diamine with refined molten hexamethylenediamine counter-currently in a fourth zone, recycling at least a portion of the diamine used to wash the crystals to said first zone, melting the washed crystals of hexamethylenediamine to provide the said refined hexamethylenediamine wash and thereafter recovering that portion of the melted crystals of hexamethylenediamines which are not used for said wash.

6. The process of claim 5 wherein the ammonia which is volatilized in the second zone is recycled to the first zone.

7. The process of claim 5 wherein molten crude hexamethylenediamine feed is introduced into the third zone and contacted with said crystalline hexamethylenediamine.

8. The process of claim 7 wherein the impurities are removed from the process along with a portion of the molten hexamethylenediamine from the third zone.

* * * * *